United States Patent [19]

Jäger et al.

[11] Patent Number: 4,469,902
[45] Date of Patent: Sep. 4, 1984

[54] 1-IODOPROP-1-YN-3-OLS AS PLANT PROTECTION AGENTS

[75] Inventors: Gerhard Jäger, Leverkusen; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 378,308

[22] Filed: Jun. 14, 1982

[30] Foreign Application Priority Data

Jun. 4, 1981 [DE] Fed. Rep. of Germany ....... 3122177

[51] Int. Cl.³ .............................................. C07C 33/48
[52] U.S. Cl. .................... 568/812; 568/813; 568/713; 424/341; 424/345
[58] Field of Search ...................... 568/812, 713, 813; 424/341, 345

[56] References Cited

U.S. PATENT DOCUMENTS

| | | |
|---|---|---|
| 1,841,768 | 1/1932 | Straus et al. |
| 2,989,568 | 6/1951 | Russell et al. .................. 568/813 |
| 3,506,682 | 4/1970 | Fried ................................. 568/813 |
| 3,929,906 | 12/1975 | Anderson ......................... 568/812 |
| 4,032,580 | 6/1977 | Galantay ........................... 568/812 |
| 4,317,672 | 3/1982 | Griffin et al. .................... 568/812 |
| 4,322,442 | 3/1982 | Jager et al. ....................... 568/812 |

FOREIGN PATENT DOCUMENTS

| | | |
|---|---|---|
| 2476 | 6/1979 | European Pat. Off. |
| 2679 | 7/1979 | European Pat. Off. ............ 568/813 |
| 913365 | 9/1946 | France ............................... 568/813 |
| 1474706 | 3/1967 | France ............................... 568/813 |
| 601151 | 6/1978 | Switzerland ....................... 568/812 |
| 1083936 | 9/1967 | United Kingdom ............... 568/813 |

Primary Examiner—Werren B. Lone
Attorney, Agent, or Firm—Sprung Horn Kramer & Woods

[57] ABSTRACT

Novel 1-iodoprop-1-yn-3-ols of the formula

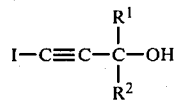

in which
$R^1$ represents optionally substituted aryl and
$R^2$ represents alkyl or cycloalkyl, which may be used as plant protection agents, especially as fungicides, are obtained when 1-iodoprop-1-yn-3-ols are reacted with iodine in the presence of a basic compound.

9 Claims, No Drawings

1-IODOPROP-1-YN-3-OLS AS PLANT PROTECTION AGENTS

The present invention relates to certain new 1-iodoprop-1-yn-3-ols, to a process for their preparation and to their use as plant protection agents.

It has already been disclosed that certain diarylalkynols, for example 3-(4-biphenyl-1-yl)-3-(3-chlorophenyl)-1-iodoprop-1-yn-3-ol, 3-(2-fluorophenyl)-1-iodo-3-phenylprop-1-yn-3-ol or 3,3-diphenyl-1-iodoprop-1-yn-3-ol, have fungicidal properties (see U.S. Pat. Ser. No. 184,694, filed Sept. 8, 1980, now pending.)

However, their activity is not always completely satisfactory, particularly when small amounts and low concentrations are used.

The present invention now provides, as new compounds, the 1-iodoprop-1-yn-3-ols of the general formula

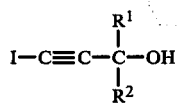

in which
R$^1$ represents optionally substituted aryl and
R$^2$ represents alkyl or cycloalkyl.

The invention also provides a process for the preparation of a 1-iodoprop-1-yn-3-ol of the formula (I), characterized in that a prop-1-yn-3-ol of the general formula $$H-C\equiv C-\underset{\underset{R^2}{|}}{\overset{\overset{R^1}{|}}{C}}-OH, \quad (II)$$

in which
R$^1$ and R$^2$ have the meanings given under formula (I), is reacted with iodine in the presence of a basic compound and, if appropriate, in the presence of a diluent.

The compounds of the formula (I) have powerful fungicidal properties. Surprisingly, the 1-iodoprop-1-yn-3-ols according to the invention exhibit a considerably greater fungicidal action than the known diarylalkynols. The active compounds according to the invention thus represent an enrichment of the art.

Formula (I) gives a general definition of the 1-iodoprop-1-yn-3-ols according to the invention. In this formula,
R$^1$ preferably represents optionally substituted aryl having 6 to 10 C atoms and
R$^2$ preferably represents straight-chain or branched alkyl having 1 to 6 C atoms, or cycloalkyl having 3 to 6 C atoms.

Azolyl, such as 1,2,4-triazol-1-yl and imidazol-1-yl, halogen, such as fluorine, chlorine, bromine and iodine, and halogenalkoxy and halogenoalkylthio, each having 1 to 2 C atoms and 1 to 5 halogen atoms, may be mentioned as preferred substituents.

1-Iodoprop-1-yn-3-ols of the formula (I), in which
R$^1$ represents optionally substituted phenyl and
R$^2$ represents methyl, ethyl, iso-propyl, n-propyl, n-butyl, sec.-butyl, tert.-butyl or cyclohexyl, are particularly preferred.

Halogen, such as fluorine and chlorine, trifluoromethoxy, trifluoromercapto, 1,2,4-triazol-1-yl and imidazol-1-yl are particularly preferred substituents.

In addition to the compounds mentioned later in the preparative examples, the compounds of the general formula (I) in the following table may be mentioned in particular:

TABLE 1

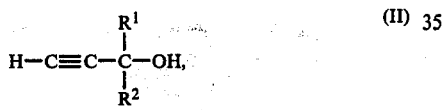

| R$^1$ | R$^2$ |
|---|---|
| Cl—⟨phenyl⟩— | —C$_2$H$_5$ |
| Cl—⟨phenyl⟩— | —nC$_3$H$_7$ |
| Cl—⟨phenyl⟩— | —nC$_4$H$_9$ |
| ⟨phenyl⟩— | —C(CH$_3$)$_3$ |
| F—⟨phenyl⟩— | —nC$_3$H$_7$ |
| F—⟨phenyl⟩— | —CH$_3$ |
| F—⟨phenyl⟩— | —C$_2$H$_5$ |
| F—⟨phenyl⟩— | —nC$_4$H$_9$ |
| F—⟨phenyl⟩— | —sec.C$_4$H$_9$ |
| Cl—⟨phenyl⟩—Cl | —C$_2$H$_5$ |

TABLE 1-continued $$\text{I}-\text{C}\equiv\text{C}-\underset{\underset{R^2}{|}}{\overset{\overset{R^1}{|}}{\text{C}}}-\text{OH} \quad (I)$$

| $R^1$ | $R^2$ |
|---|---|
| 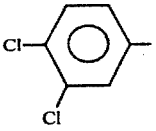 | —nC$_3$H$_7$ |
| 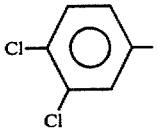 | —iC$_3$H$_7$ |
| 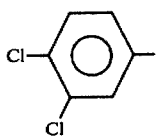 | —nC$_4$H$_9$ |
| 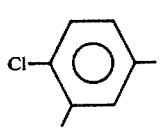 | —tert.C$_4$H$_9$ |
|  | —C$_2$H$_5$ |
| 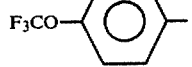 | —tert.C$_4$H$_9$ |
| 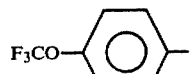 | —tert.C$_4$H$_9$ |
|  | —C$_2$H$_5$ |
|  | —C$_2$H$_5$ |
| 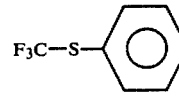 | —C$_3$H$_7$ |
| 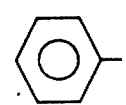 | 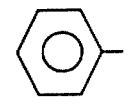 |

TABLE 1-continued $$\text{I}-\text{C}\equiv\text{C}-\underset{\underset{R^2}{|}}{\overset{\overset{R^1}{|}}{\text{C}}}-\text{OH} \quad (I)$$

| $R^1$ | $R^2$ |
|---|---|
| 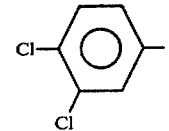 | 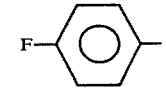 |
| 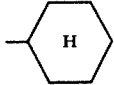 | 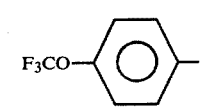 |
| 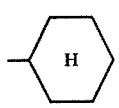 | 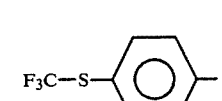 |
| 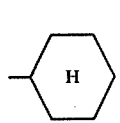 | 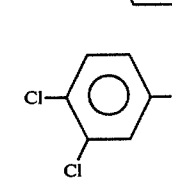 |
|  | —C$_2$H$_5$ |
| 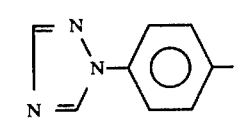 | —C$_3$H$_7$ |
| 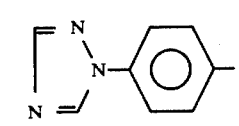 | 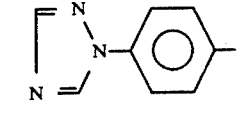 |
| 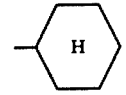 | —C$_2$H$_5$ |
| 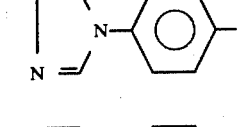 | 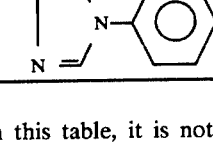 |

In this table, it is not intended to exclude possible combinations of any desired radicals $R^1$ with any desired radicals $R^2$, which fall within the definition of the general formula (I).

If, for example, 3-(4-trifluoromethoxyphenyl)-but-1-yn-3-ol and iodine are used as starting materials, the course of the reaction can be represented by the following equation:

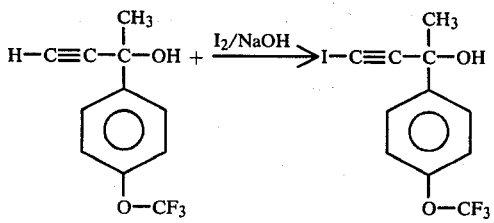

Formula (II) gives a general definition of the prop-1-yn-3-ols employed as starting materials in carrying out the process according to the invention. In this formula, $R^1$ preferably represents optionally substituted aryl having 6 to 10 C atoms and $R^2$ preferably represents straight-chain or branched alkyl having 1 to 6 C atoms, or cycloalkyl having 3 to 6 C atoms.

Azolyl, such as 1,2,4-triazol-1-yl and imidazol-1-yl, halogen, such as fluorine, chlorine, bromine and iodine, and halogenoalkoxy and halogenoalkylthio, each having 1 to 2 C atoms and 1 to 5 halogen atoms, may be mentioned as substituents.

1-Iodoprop-1-yn-3-ols of the formula (I) in which $R^1$ represents optionally substituted phenyl and $R^2$ represents methyl, ethyl, iso-propyl, n-propyl, n-butyl, sec.-butyl, tert.-butyl or cyclohexyl, are particularly preferred.

Halogen, such as fluorine and chlorine, trifluoromethoxy, trifluoromercapto, 1,2,4-triazol-1-yl and imidazol-1-yl are particularly preferred substituents.

The prop-1-yn-3-ols of the formula (II) are known and/or can be prepared according to processes which are in themselves known (DE-OS (German Published Specification) No. 2,438,462).

They are obtained, for example, by ethynylation of the corresponding ketones with mono-alkali metal salts or mono-Grignard compounds of acetylene in suitable solvents and subsequent hydrolysis. Thus, the compounds of the formula (II) can be prepared by reacting the appropriate ketone with acetylene in the presence of an alkali metal salt of a tertiary alcohol in an aprotic solvent, or by adding the ketone to an alkali metal acetylide solution prepared from an alkali metal and acetylene in liquid ammonia.

Furthermore, the compounds of the formula (II) can be prepared, for example, by reacting acetylene-magnesium halides with the appropriate ketones in an aprotic solvent, for example diethyl ether or tetrahydrofuran. The acetylene-magnesium halides are obtained by passing acetylene into solutions of alkyl-magnesium halides.

The process according to the invention can be carried out in a diluent. A protic solvent, for example an alcohol, such as methanol, ethanol, propanol, isopropanol and glycol monomethyl ether, can be employed as the diluent. If appropriate, mixtures with other diluents, such as water or organic amines, such as pyridine, quinoline or picolines, can also be employed.

The reaction according to the invention is carried out in the presence of a basic compound. An alkaline earth metal hydroxide or alkali metal hydroxide is preferably employed, and an aqueous solution of sodium hydroxide or potassium hydroxide is particularly preferably employed.

In the process according to the invention, the reaction temperatures can be varied within a relatively wide range. In general, the reaction is carried out at from 0° to 50° C., preferably at from 10° to 30° C.

In carrying out the process according to the invention, iodine and the aqueous alkali metal hydroxide solution can be added simultaneously to the prop-1-yn-3-ol of the formula (II). However, it is also possible to combine simultaneously the prop-1-yn-3-ol of the formula (II), iodine and an aqueous alkali metal hydroxide solution.

In general, the reactants are employed in stoichiometric amounts. In particular cases, it can be advantageous to employ a reactant in excess.

The process according to the invention can be carried out as follows: prop-1-yn-3-ol of the formula (II) is introduced initially. The basic compound is added to it, and iodine is introduced simultaneously.

After the end of the reaction, water is generally added to the reaction mixture. The resulting 1-iodoprop-1-yn-3-ol can then be isolated in a customary manner and can be purified, if appropriate, by crystallization or distillation.

The prop-1-yn-3-ols of the formula (II) employed in the process according to the invention can contain an asymmetric C atom. In particular cases, the configuration of this C atom can be influenced in the preparation of the 1-iodoprop-1-yn-3-ols of the formula (I).

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as against the apple scab causative organism (*Fusicladium dendriticum*); and also for combating cereal diseases such as brown leaf rust of wheat (*Puccinia recondita*).

When used in appropriate concentrations, the active compounds according to the invention also exhibit bactericidal and acaricidal actions.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphates, aryl sulphonates as well as albumin hydrolysis products. Dispersing agents include, for for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such, in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general between 1 and 0.0001% by weight, preferably between 0.5 and 0.001%.

In the treatment of seed, amounts of active compound of in general 0.001 to 50 g per kilogram of seed, preferably 0.01 to 10 g, are employed.

For the treatment of soil, active compound concentrations of in general 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(a) 3-(4-Trifluoromethoxyphenyl)-but-1-yn-3-ol

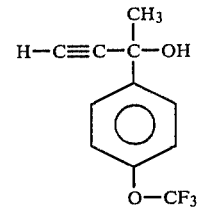

A moderate stream of acetylene was passed for 30 minutes through a suspension of 47 g (0.42 mol) of potassium tert.-butylate in 500 ml of tetrahydrofuran at 15° C. A solution of 62.5 g (0.3 mol) of 4-trifluoromethoxyacetophenone in 100 ml of tetrahydrofuran was then added dropwise in the course of one hour, the passage of acetylene being continued. When two hours had elapsed after the end of the addition of the ketone, the solution was acidified with 2N hydrochloric acid, with external cooling, precipitated salt was filtered off, and the filtrate was concentrated by evaporation under reduced pressure. The oily residue was taken up in 250 ml of ethyl acetate, and the organic phase was washed three times with 50 ml of water, dried over anhydrous sodium sulphate and concentrated by evaporation in vacuo. Remaining solvent was removed from the liquid residue at 50° C. under 0.01 mbar. 61.6 g (89.2% of theory) of a yellowish oil of refractive index $n_D^{20} = 1.4659$ were obtained.

(b) 1-Iodo-3-(4-trifluoromethoxyphenyl)-but-1-yn-3-ol

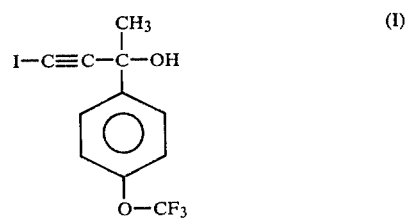

40 ml of concentrated sodium hydroxide solution were added dropwise to a solution of 23 g (0.1 mol) of 3-(4-trifluoromethoxyphenyl)-but-1-yn-3-ol in 250 ml of methanol at 15°-20° C. in the course of 30 minutes, while stirring, and 25.4 g (0.1 mol) of iodine were simultaneously introduced in portions. After three hours, the reaction mixture was stirred into 1,000 ml of water. The initially oil reaction product crystallized on standing. The solid material was taken up in 200 ml of ethyl acetate, the solution was washed twice with 100 ml of water, and the organic phase was dried over anhydrous sodium sulphate and concentrated by evaporation under reduced pressure. The residual oil was dissolved in a small quantity of petroleum ether, the solution was cooled and the precipitated crystals were filtered off under suction. 17.2 g (=48.2% of theory) of colorless crystals of melting point 75°-76° C. were obtained.

The following compounds of the general formula $$I-C\equiv C-\overset{R^1}{\underset{R^2}{C}}-OH \quad (I)$$

were obtained in a manner analogous to that described in Example 1

TABLE 2

| Compound No. | R¹ | R² | Physical constants |
|---|---|---|---|
| 2 | 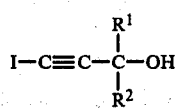 | —CH₃ | m.p: 72–74° C. |
| 3 | F—⌬— | —CH(CH₃)₂ | m.p: 57–59° C. |
| 4 | [triazolyl-phenyl] | —CH₃ | m.p: 157–59° C. |
| 5 | [triazolyl-phenyl isomer] | —CH₃ | m.p: 177–79° C. |
| 6 | Cl—⌬— | —CH(CH₃)₂ | $n_D^{20} = 1.593$ |
| 7 | ⌬— | —CH₃ | $n_D^{20} = 1.5661$ |
| 8 | Cl—⌬— | —CH₃ | m.p: 84–85° C. |

TABLE 2-continued

| Compound No. | R¹ | R² | Physical constants |
|---|---|---|---|
| 9 | 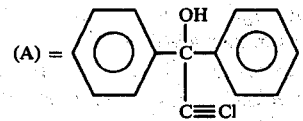 | —CH₃ | $n_D^{20} = 1.521$ |
| 10 | ⌬— | 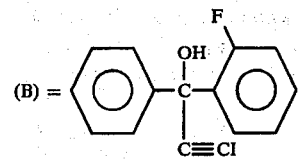 | $n_D^{20} = 1.565$ |

Use Examples

The fungicidal activity of the compounds of this invention is illustrated by the following biotest examples.

In these examples, the compounds according to the present invention are each identified by the number (given in brackets) from Example 1 and Table 2.

The known comparison compounds are identified as follows:

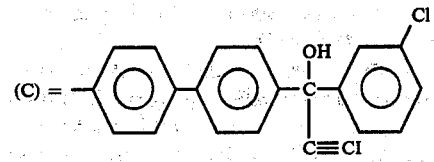

3,3-Diphenyl-1-iodo-prop-1-yn-3-ol (B) = [structure]

3-(2-Fluorphenyl)-1-iodo-3-phenylprop-1-yn-3-ol (C) = [structure]

3-(4-Biphenyl-1-yl)-3-(3-(chlorophenyl)-1-iodo-prop-1-yn-3-ol.

Example 2

Fusicladium test (apple)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants were then again brought into a greenhouse for 14 days.

15 days after inoculation, the infection of the seedlings was determined. The assessment data were converted to percent infection. 0% denoted no infection and 100% denoted that the plants were totally infected.

In this test, a clearly superior activity compared with the prior art was shown, for example, by the compound (2).

Example 3

Puccinia Test (wheat)/protective
Solvent: 100 parts by weight of dimethylformamide
Emulsifier: 0.25 part by weight of alkyl-aryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were inoculated with a spore suspension of *Puccinia recondita* in a 0.1% strength aqueous agar solution. After the spore suspension had dried on, the plants were sprayed with the preparation of active compound until dew-moist. The plants remained in an incubation chamber at 20° C. and 100% relative atmospheric humidity for 24 hours.

The plants were placed in a greenhouse at a temperature of about 20° C. and a relative atmospheric humidity of about 80% in order to promote the development of rust pustules.

Evaluation was carried out 10 days after the inoculation.

In this test, a clearly superior activity compared with the prior art was shown, for example, by the compounds (2), (8) and (6).

It will be appreciated that the instant specification and examples are set forth by way of illustration and not limitation, and that various modifications and changes may be made without departing from the spirit and scope of the present invention.

We claim:
1. A 1-iodoprop-1-yn-3-ol of the formula

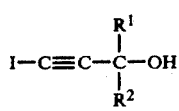

in which
R$^1$ is optionally substituted aryl, and
R$^2$ is alkyl or cycloalkyl.

2. A compound according to claim 1, in which
R$^1$ is optionally substituted aryl having 6 to 10 C atoms, and R$^2$ is alkyl having 1 to 6 C atoms, or cycloalkyl having 3 to 6 C atoms.

3. A compound according to claim 1, in which
R$^1$ is phenyl optionally substituted by at least one of azolyl, halogen and halogenoalkoxy and halogenoalkylthio radicals each with 1 or 2 C atoms and 1 to 5 halogen atoms, and R$^2$ is methyl, ethyl, iso-propyl, n-propyl, n-butyl, sec.-butyl, tert.-butyl or cyclohexyl.

4. A compound according to claim 1, wherein such compound is 1-iodo-3-(3,4-dichlorophenyl)-but-1-yn-3-ol of the formula

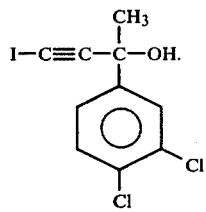

5. A compound according to claim 1, wherein such compound is 1-iodo-3-(4-chlorophenyl)-4-methyl-pent-1-yn-3-ol of the formula

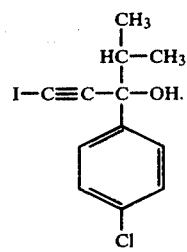

6. A compound according to claim 1, wherein such compound is 1-iodo-3-(4-chlorophenyl)-but-1-yn-3-ol of the formula

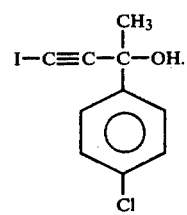

7. A fungicidal composition comprising a fungicidally effective amount of a compound according to claim 1 in admixture with a diluent.

8. A method of combating fungi comprising applying to the fungi, or to a habitat thereof, a fungicidally effective amount of a compound according to claim 1.

9. The method according to claim 8, wherein such compound is
1-iodo-3-(3,4-dichlorophenyl)-but-1-yn-3-ol;
1-iodo-3-(4-chlorophenyl)-4-methyl-pent-1-yn-3-ol; or
1-iodo-3-(4-chlorophenyl)-but-1-yn-3-ol.

* * * * *

UNITED STATES PATENT AND TRADEMARK OFFICE
CERTIFICATE OF CORRECTION

PATENT NO. : 4,469,902

DATED : September 4, 1984

INVENTOR(S) : Gerhard Jager

It is certified that error appears in the above-identified patent and that said Letters Patent is hereby corrected as shown below:

| | |
|---|---|
| Title on 1st page and Col. 1 | Beginning of title insert --NOVEL-- |
| 1st page, No. 75 "Inventors:" | Delete in its entirety and substitute --Gerhard Jäger, Leverkusen, Fed. Rep. of Germany-- |
| No. 22, "Filed:" | Delete "Jun. 14, 1982" and substitute --May 14, 1982-- |
| Col. 1, line 60 | Delete "halogenalkoxy" and substitute --halogenoalkoxy-- |
| Col. 9, line 6 | Delete "oil" and substitute --oily-- |

Signed and Sealed this

Ninth Day of July 1985

[SEAL]

Attest:

DONALD J. QUIGG

Attesting Officer

Acting Commissioner of Patents and Trademarks